(12) United States Patent
Srinivasan

(10) Patent No.: US 11,607,324 B2
(45) Date of Patent: Mar. 21, 2023

(54) PROSTHETIC LEG COMPRISING THREE-DIMENSIONALLY PRINTED ELEMENTS

(71) Applicant: Suraj Srinivasan, San Diego, CA (US)

(72) Inventor: Suraj Srinivasan, San Diego, CA (US)

( * ) Notice: Subject to any disclaimer, the term of this patent is extended or adjusted under 35 U.S.C. 154(b) by 0 days.

(21) Appl. No.: 17/070,151

(22) Filed: Oct. 14, 2020

(65) Prior Publication Data

US 2021/0212842 A1 Jul. 15, 2021

Related U.S. Application Data

(62) Division of application No. 16/167,283, filed on Oct. 22, 2018, now abandoned.

(51) Int. Cl.
*A61F 2/66* (2006.01)
*A61F 2/64* (2006.01)
(Continued)

(52) U.S. Cl.
CPC .............. *A61F 2/60* (2013.01); *A61F 2/5046* (2013.01); *A61F 2/54* (2013.01); *A61F 2/583* (2013.01); *A61F 2/586* (2013.01); *A61F 2/601* (2013.01); *A61F 2/64* (2013.01); *A61F 2/6607* (2013.01); *A61F 2/68* (2013.01); *A61F 2/70* (2013.01); *A61F 2/80* (2013.01); *A61F 2/3094* (2013.01); *A61F 2002/3096* (2013.01); *A61F 2002/502* (2013.01); *A61F 2002/505* (2013.01); *A61F 2002/5009* (2013.01); *A61F 2002/5049* (2013.01); *A61F 2002/5053* (2013.01); *A61F 2002/5069* (2013.01); *A61F 2002/5079* (2013.01); *A61F 2002/5083* (2013.01); *A61F 2002/5093* (2013.01); *A61F 2002/5096* (2013.01); *A61F 2002/5098* (2013.01); *A61F 2002/587* (2013.01); *A61F 2002/607* (2013.01); *A61F 2002/608* (2013.01); *A61F 2002/6854* (2013.01); *A61F 2002/701* (2013.01);
(Continued)

(58) Field of Classification Search
CPC ........ A61F 2002/5096–5098; A61F 2002/502; A61F 2002/5029; A61F 2002/5083
See application file for complete search history.

(56) References Cited

U.S. PATENT DOCUMENTS

2018/0289511 A1* 10/2018 Fairley ...................... A61F 2/64

OTHER PUBLICATIONS

U.S. Appl. No. 62/483,372, filed Apr. 8, 2017.*

* cited by examiner

*Primary Examiner* — David H Willse

(57) ABSTRACT

A prosthetic appendage for attachment to an outer extremity of an amputated limb that is composed of modular elements fabricated by three-dimensional printing. In one embodiment the prosthetic appendage is a leg. The prosthetic leg includes a foot portion and a plurality of modular and three-dimensionally printed limb elements. One of the plurality of limb elements is pivotally coupled to the foot portion and another of the limb elements is configured at one end to receive the outer extremity of the amputated leg. In another embodiment of the present invention the prosthetic appendage is a hand. The prosthetic hand includes a wrist element with one end configured to receive the outer extremity of an amputated hand, a base portion attached to the wrist element and a plurality of modular and three-dimensionally printed finger elements selectively coupled to adjacent finger elements or the base to form prosthetic fingers.

9 Claims, 16 Drawing Sheets

(51) Int. Cl.
*A61F 2/80* (2006.01)
*A61F 2/62* (2006.01)
*A61F 2/60* (2006.01)
*A61F 2/50* (2006.01)
*A61F 2/54* (2006.01)
*A61F 2/58* (2006.01)
*A61F 2/68* (2006.01)
*A61F 2/70* (2006.01)
A61F 2/30 (2006.01)
B33Y 80/00 (2015.01)
A61F 2/76 (2006.01)

(52) U.S. Cl.
CPC ... *A61F 2002/704* (2013.01); *A61F 2002/707* (2013.01); *A61F 2002/7635* (2013.01); *B33Y 80/00* (2014.12)

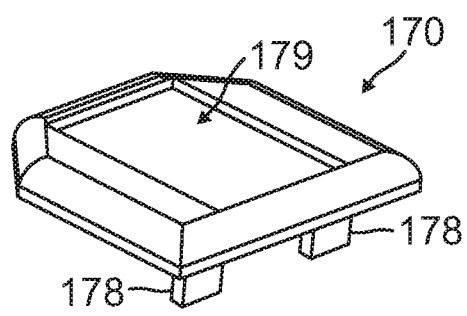
FIG. 16a
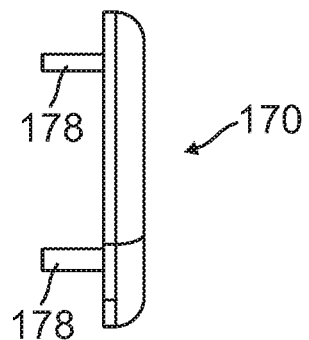
FIG. 16b
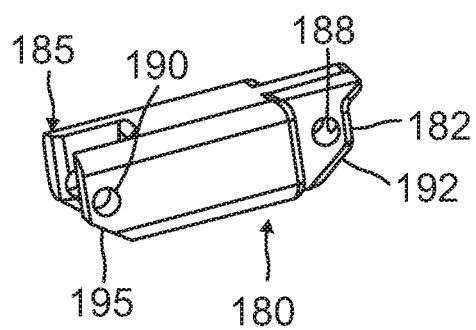
FIG. 17a
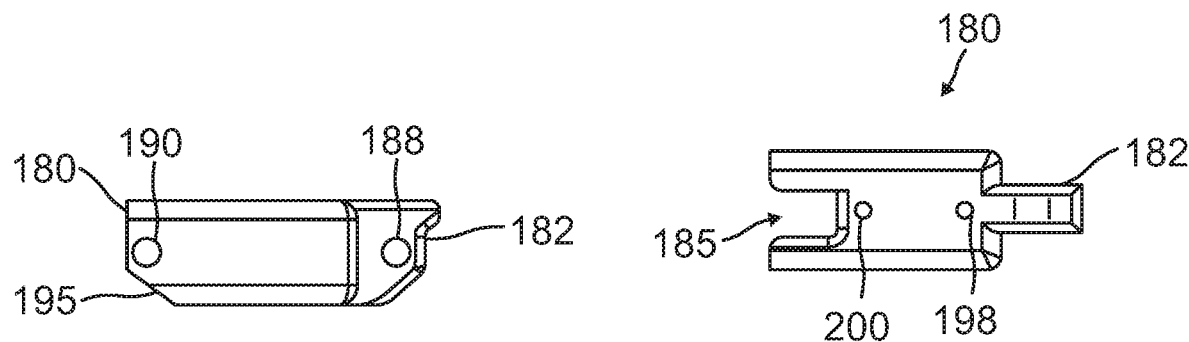
FIG. 17b
FIG. 17c

PROSTHETIC LEG COMPRISING THREE-DIMENSIONALLY PRINTED ELEMENTS

BACKGROUND OF THE INVENTION

The present invention pertains generally to prosthetic limbs and, more particularly, to prosthetic hands and prosthetic legs.

The use of prosthetics has a long history dating back some three thousand years to wooden toes found on Egyptian mummies. Prosthetic limbs are rife in literature from Captain Ahab's wooden leg in "Moby Dick" to Captain Hook's eponymous appendage in "Peter Pan". A prosthetic limb replaces a missing extremity, such as an arm or leg and may be needed for a variety of reasons including accidents and disease. An artificial limb may also be needed when a person is born with a missing or damaged limb. The type of prosthetic limb to be used is largely determined by the extent of amputation and the location of the missing limb. A transtibial prosthesis, for example, is an artificial leg attached to an outer extremity of a user's amputated limb below the knee. This prosthetic includes a lower leg, a foot and preferably some form of ankle joint connecting the two. In contrast, a transfemoral prosthesis is an artificial leg attached to an outer extremity of a user's amputated limb above the knee. In addition to the elements of a transtibial prosthesis, a transfemoral prosthesis further includes an upper leg portion and preferably some form of knee joint. A transradial prosthesis is an artificial hand that is attached to an outer extremity of a user's amputated limb below the elbow. This prosthetic includes a lower arm or wrist portion and some form of artificial hand structure.

One problem with existing prosthetic limbs is that they are not readily available to people living in remote or developing parts of the world. Many amputees in developing areas of the world, including large portions of Africa, lack access to prosthetic limb manufacturers and often do not have the financial resources to purchase them. Most modern prosthetic limbs require custom fitting such that the user needs to be present at a location where such measurements can be performed. Extensive procedures are typically required to cast a negative mold of the outer extremity of a user's amputated limb in order to make an appropriate interface between the prosthetic limb and the outer extremity of the user's amputated limb. An actual interface is then made with this mold and typically must be custom made, thereby significantly increasing the cost and time to make the prosthetic limb available to an individual user. Additional steps to match a user's height with an appropriate length of prosthetic limb normally requires still further fitting, alignment and integration. Without access to an appropriate facility or resources to pay for a such prosthetic limb, many amputees in remote locations and developing countries cannot obtain properly designed prosthetic limbs and may be forced to rely instead upon other devices for mobility, such as crutches.

Various prosthetic limbs based upon materials such as wood, fiberglass and bamboo exist in the market today, but these devices tend to be heavy and require substantial custom fitting and adjustment. More sophisticated models also exist, and adjust well to a user, but tend to be prohibitive in terms of the costs to both manufacture and customize to an individual user.

Another deficiency of conventional prosthetic limbs is that the entire prosthetic limb typically has to be replaced if a single component experiences a break. The present invention addresses these and other deficiencies.

BRIEF SUMMARY OF THE INVENTION

It is an object of the present invention to provide a prosthetic limb suitable for use in remote locations. It is a further object of the present invention to provide a prosthetic limb capable of being manufactured at substantially reduced cost. A still further aspect of invention is to provide a prosthetic limb that does not require complete replacement of the prosthetic if a single component fails.

These and other aspects of the present invention are achieved by, among other things, fabricating the prosthetic limb from modular and three-dimensionally printed components. In one embodiment a prosthetic leg is provided for attachment to an outer extremity of an amputated leg including a foot element, a plurality of modular three-dimensionally printed limb elements forming a protrusion at a first end and a recess at a second and opposing end, the recess being configured to receive a protrusion from an adjacent three-dimensionally printed component, with at least one of the three-dimensionally printed limb elements being pivotally attached to the foot element and at least another of the three-dimensionally printed limb elements forming a cavity configured to receive the outer extremity of an amputated leg.

In a further embodiment of the present invention a prosthetic knee structure is added to the above structure. This prosthetic knee includes a first three dimensionally printed knee element that forms at a first end a ridge and at a second and opposing end forms a protrusion or recess to engage an adjacent one of the plurality of limb elements. This first knee element further defines a plurality of apertures at the first end and in a side surface of the first knee element, the apertures at the first end communicating with the apertures formed in the side. This knee structure further includes a second three-dimensionally printed knee element forming at a first end a pair of ridges spaced apart to slidingly receive the ridge of the first knee element and forming at a second and opposing end a protrusion or recess to engage an adjacent one of the plurality of limb elements. A sliding engagement of the ridge of the first knee element between the pair of ridges of the second knee element affords relative motion between the first and second knee elements in generally a single plane. This second knee element further defines a plurality of apertures at the first end and in a side of the second knee element with the apertures in the first end communicating with the apertures in the side. This further embodiment further includes a plurality of winding elements respectively and detachably connected to the first and second knee elements. A plurality of flexible and non-extensible connectors are attached at opposing ends to pairs of the winding elements, a first connector of the pair being detachably connected to the first knee element and a second connector of a pair being detachably connected to the second knee element; the connectors being further threaded through the apertures of the first and second knee elements. With this structural arrangement relative motion of the first and second knee elements is prohibited when the flexible connectors are tensioned and relative motion of the first and second knee elements is permitted when the flexible connectors are slack.

In yet another embodiment of the present invention a prosthetic hand for attachment is provided for attachment to an outer extremity of an amputated hand. In this embodiment the prosthetic hand includes a three-dimensionally printed wrist element having one end configured to receive the outer extremity of the amputated hand, a three-dimensionally printed base element attached at one end to the wrist element, a first plurality of three-dimensionally printed finger elements each pivotally coupled to adjacent finger elements, each finger element defining a first aperture extending through the finger element and further defining a pair of apertures on one side of the finger elements at opposing ends of the finger element. In this embodiment at least one of the finger elements is pivotally coupled to the base element. This embodiment further includes a first flexible connector having a first portion attached at a first end to the base element, threaded internally through the plurality of finger elements and a second portion exiting a first finger element and entering an adjacent second finger element through adjacent apertures in the sides of the adjacent finger elements. An actuator is included and mounted on the base element. The actuator has a mobile element attached to a second end of the first flexible connector so that activation of the actuator causes displacement of the flexible connector with respect to the base portion and causes the first plurality of finger elements to pivot with respect to the base portion and with respect to one another thereby opening or closing the first plurality finger elements. A controller configured to activate and deactivate the actuator is included in this embodiment.

In still a further embodiment of the present invention a thumb structure is provided for the prosthetic hand. This thumb structure includes a second plurality of three dimensionally printed thumb elements, each thumb element defining a first aperture extending through the thumb element and further defining a pair of apertures on one side of the thumb elements at opposing ends of the thumb elements At least one of the thumb elements is pivotally coupled to the base element to pivot in a plane generally perpendicular to a pivot plane of the first plurality of three-dimensionally printed finger elements. A second flexible connector having a first portion attached at a first end to the base element is provided and threaded internally through the plurality of thumb elements with a second portion of the flexible connector disposed to exit a first thumb element and enter an adjacent second thumb element through adjacent apertures in the sides of the adjacent thumb elements. This second portion is further attached at a second end to the actuator. Activation of the actuator causes displacement of the second flexible connector with respect to the base portion and causes the second plurality of thumb elements to pivot with respect to the palm portion and with respect to one another thereby opening or closing the second plurality of thumb elements.

The foregoing and further advantages, features and principles of the present invention will become more readily apparent from the following detailed description of several preferred embodiments of the present invention that follows below with reference to the accompanying drawings.

BRIEF DESCRIPTION OF THE DRAWINGS

FIG. 6b is a top down view of the locking element depicted in FIG. 6a.

FIG. 11b is a top down view of the winding element depicted in FIG. 11a.

FIG. 12b is an expanded side view of the knee element depicted in FIG. 12a.

FIG. 16a is a perspective view of a cover element for the prosthetic hand depicted in FIGS. 13 and 14.

FIG. 16b is a side view of the cover element depicted in FIG. 16a.

FIG. 17a is a perspective view of a three-dimensionally printed modular finger element for the prosthetic hand depicted in FIGS. 13 and 14.

FIG. 17b is a side view of the modular finger element depicted in FIG. 17a.

FIG. 17c is a bottom up view of the modular finger element depicted in FIGS. 17a and 17b.

DETAILED DESCRIPTION

Figure 1:
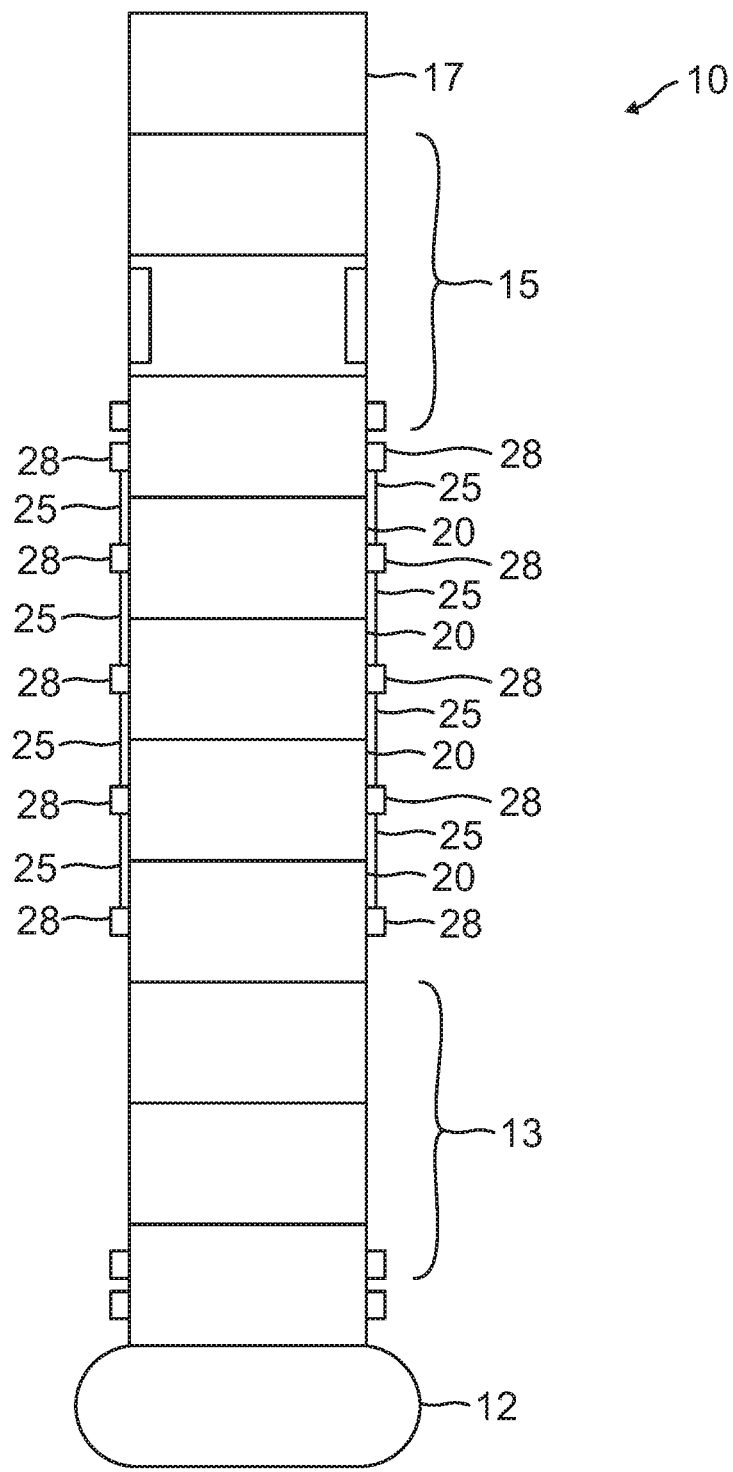
FIG. 1 is a forward view of a transfemoral leg prosthesis in accordance with an embodiment of the present invention.

Referring to the figures, and more particularly FIG. 1 thereof, there is shown a transfemoral leg prosthesis 10 in accordance with an embodiment of the present invention. As shown, the leg prosthesis 10 includes a foot element 12, an ankle joint 13, a knee joint 15, a limb receiving element 18 configured to receive an outer extremity of an amputated leg and a plurality of essentially identical modular limb elements 20 disposed between the ankle joint 13 and the knee joint 15. In order to accommodate the specific length of the outer extremity of an amputated leg on a specific user, additional modular elements 20 may be disposed between the limb receiving element 18 and the knee joint 15 or between the ankle joint 13 and the knee joint 15. The degree of user customization achievable by simply altering the number of modular elements 20 is dependent upon the overall length of the modular elements. Inventor has found that a length of one inch (1.0") affords an optimal degree of customization for users by adding or subtracting the number of modular elements comprising the leg prosthesis 10.

In an alternative embodiment of the present invention intended for use as a transtibial leg prosthesis the knee joint 15 would not be present and the limb receiving element 18 would instead be attached to a top end of the plurality of modular limb elements 20. In one embodiment of the present invention further illustrated in FIG. 1 a plurality of flexible and non-extensible connectors 25 are disposed across adjacent modular limb elements 20 to secure adjacent modular limb elements to one another. The flexible connectors 25 are secured proximate opposing ends thereof to tensioning elements 28 which are in turn attached to exterior surfaces of the modular limb elements 20. As shown in FIG. 1, two flexible connectors 25 may be disposed on opposing sides of the modular limb elements 20 to advantageously secure adjacent modular limb elements 20. Alternatively, if desired, a greater number of connectors may be disposed at generally equilateral angles about the sides of the modular limb elements 18. The flexible connectors 25 may be composed of several different materials. In one embodiment of the present invention the flexible connectors 25 are composed of non-extensible and high tensile strength string material such as commonly available in the market. Alternatively, the flexible connectors 25 may be composed of a non-extensible flat tape material such as are also commonly available in the market. Such tape materials have been rated to bear loads as great at two thousand pounds.

Figure 2A:
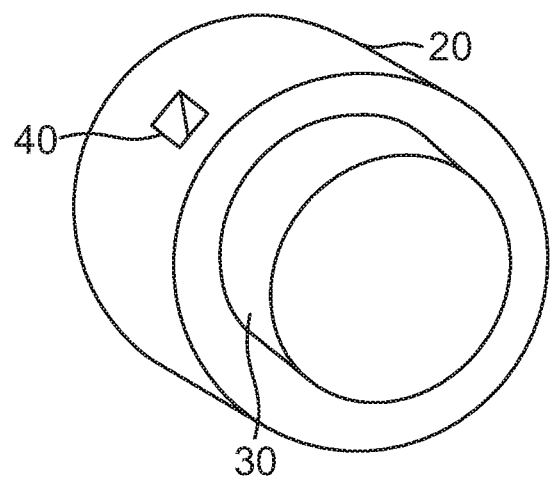
FIG. 2a is a perspective view of a first end of a modular three dimensionally printed leg element of the present invention.
Figure 2B:
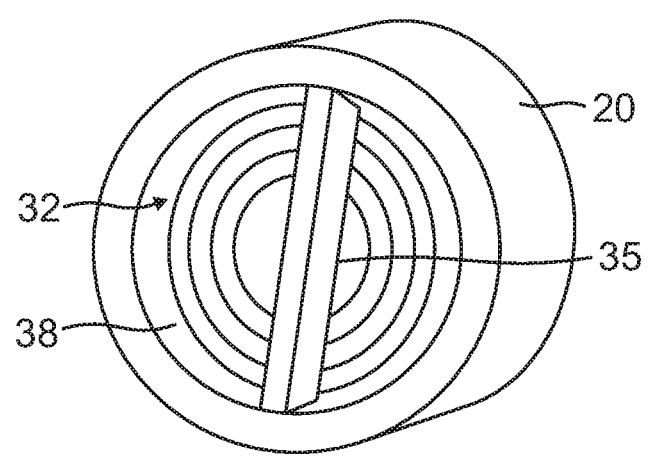
FIG. 2b is a perspective view of a second end of a modular three dimensionally printed leg element of the present invention.

An individual modular leg element 20 is shown in FIGS. 2a and 2b. The modular leg element 20, foot element 12, ankle joint 13 and knee joint 15 are all fabricated using a three-dimensional printer. One vital aspect of the present invention is the modular character of the various elements forming the leg and hand prosthesis of the present invention. Another vital aspect of the present invention is use of three-dimensional printing devices and three-dimensionally printing techniques to fabricate the modular elements comprising the prosthesis of the present invention. While three-dimension printers are known in the art and generally commercially available, three-dimensionally printing techniques and three-dimensional printers have not been used to fabricate a plurality of modular elements assembled together to form leg and hand prostheses as described and claimed herein. Several substantial advantages are achieved by use of three-dimensional printing to fabricate modular elements for leg and hand prostheses. For example, three-dimensional printing provides fabrication of modular prosthetic limb elements at a fraction of the cost of molded or cast plastics. Once a three-dimensional printer is available for use, the cost of operating the three-dimensional printer is considerably less than the cost of obtaining a die for conventional plastic molding; the latter typically costing approximately thirty thousand dollars. Additionally, once purchased the die can only be used to form additional elements having the exact same dimensions as the original element since the dimensions of the die are fixed and not subject to easy alteration. In comparison, three-dimensional printers have the capability to fabricate identically shaped elements with differing dimensions, thus allowing fabrication of prosthetic limbs in accordance with the present invention with a high degree of customization. The same modular configurations, altering only in dimensions, can be used to create individually tailored leg and hand prostheses for men, women and even children. The same certainly cannot be said of conventional die cast plastic prostheses. Additionally, because of the modular nature of the elements forming the leg and hand prostheses of the present invention, failure of any one or a few of the modular elements does not necessitate replacement of the entire prosthesis. Instead, the damaged modular elements may be removed and replaced by three-dimensionally printing a new modular element and installing the new modular element in the existing prosthetic limb at a fraction of the cost of replacing an entire conventional prosthetic limb.

The structure on the modular limb elements 20 is more fully depicted in FIG. 2. As shown, a first end of the modular limb element 20 forms a protrusion 30 and an opposing end of the modular limb element 20 forms a recess 32. The recess 32 is configured to receive the protrusion 30 from an adjacent modular limb element 20. As further shown in FIG. 2b the modular limb element 20 preferably, though not necessarily, forms a hollow interior and optionally, but advantageously, further forms a cross-bar 35 connected to an inner wall 38 of the modular limb element 20. This cross-bar is believed to enhance the structural strength of the modular limb element 20 and reduce the potential of a protrusion from an adjacent modular limb element travelling disadvantageously deeper into the recess of the modular limb element 20, thereby splitting the modular limb element 20 open. As further illustrated in FIG. 2a, a side-wall of the modular limb element 20 may define one or more apertures 40 shaped to accept the tensioning elements 28.

Figure 3:
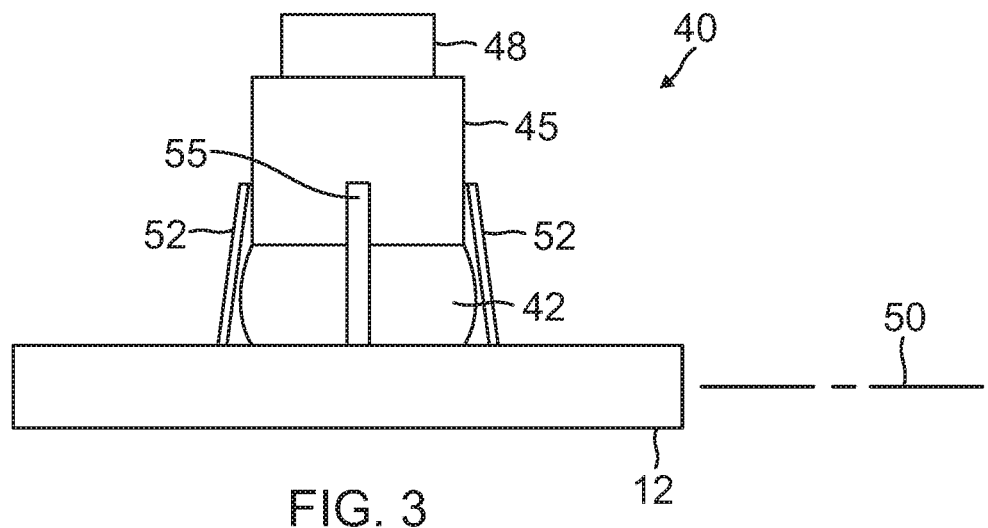
FIG. 3 is a side view of an ankle joint for a leg prosthesis in accordance with an embodiment of the present invention.
Figure 4:
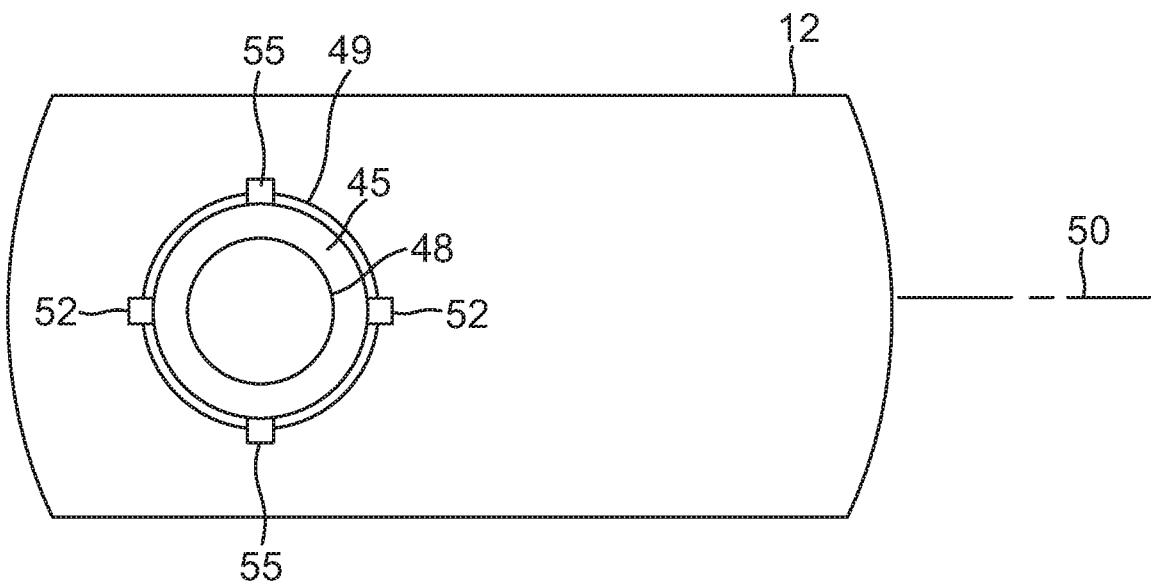
FIG. 4 is a top down view of the ankle joint depicted in FIG. 3.

Referring to FIGS. 3 and 4 there is shown an alternative embodiment 40 of the ankle joint 13. As shown, this alternative embodiment includes a generally spherical ball 42 to facilitate motion between the foot element 12 and a joint element 45 disposed adjacent the foot element 12. The joint element 45 is fabricated using a three-dimensional printer. The joint element 45 forms a recess at one end shaped to accept a portion of the ball 42. An opposing end of the joint element 45 forms a protrusion 48 configured to fit into the recess in an adjacent modular limb element 20. The foot element 12 similarly defines a depression shaped to accept a portion of the ball 42 opposite the portion of the ball disposed in the joint element 45. Pivotal motion, preferably in approximately a single plane generally parallel to a longitudinal axis 50 of the foot element 12, is achieved by inclusion of two pairs of flexible connectors respectively attached at opposing ends to the foot element 12 and the joint element 45. A first pair 52 of flexible connectors is disposed at generally opposing sides of the joint element 45 so as to form a line between themselves generally parallel to the longitudinal axis 50 of the foot element 12. This first pair of flexible connectors is composed of material that is elastically extensible. A second pair 55 of flexible connectors is disposed at generally opposing sides of the joint element 45 so as to form a line between themselves generally perpendicular to the longitudinal axis 50 of the foot element 12. This second pair of flexible connectors 55 is composed of material that is relatively inelastic and essentially non-extensible. That is, the second pair of flexible connectors 55 is composed of materials that do not stretch or, alternatively, stretch very little. In operation the elastic extension of the first pair 55 of flexible connectors facilitates relative rotational motion between the foot element 12 and the joint element 45 in a plane generally parallel to the longitudinal axis of the foot element 12 while the inelastic non-extension of the second pair 55 of flexible connectors prohibits relative rotational motion in a plane generally perpendicular to the longitudinal axis of the foot element 12.

The alternative joint embodiment 40, including a spherical ball 42, is also suitable for use as the knee joint 15, as further illustrated in Figs. Sa and Sb. In this embodiment 58 of the knee joint two joint elements 60 and 62 are configured with the structure disclosed above for joint element 45. The joint elements 60 and 62 are both fabricated using a three-dimensional printer. Each of joint elements 60 and 62 forms a recess at first ends shaped to accept a portion of a spherical ball 67. Second ends of the joint elements 60 and 62 opposite the first ends may each form protrusions, such as protrusion 68 shown in Fig. Sa, configured to fit into the recess in an adjacent modular limb element 20. Alternatively, one of joint elements 60 or 62 may instead form a recess configured to receive the protrusion 30 of a modular limb element 20. Pivotal motion, preferably in approximately a single plane generally parallel to the pivot plane of ankle joint 40, is achieved by inclusion of two pairs of flexible connectors respectively attached at opposing ends to the joint elements 60 and 62. A first pair 69 of flexible connectors is disposed at generally opposing sides of the joint elements 60 and 62 so as to form a line between themselves generally parallel to the pivot plane of ankle joint 40. This first pair of flexible connectors 69 is composed of material that is elastically extensible. A second pair 70 of flexible connectors is disposed at generally opposing sides of the joint elements 60 and 62 so as to form a line between themselves generally perpendicular to the pivot plane of ankle joint 40. This second pair of flexible connectors 70 is composed of material that is relatively inelastic and essentially non-extensible. That is, the second pair of flexible connectors 70 is composed of materials that do not stretch or, alternatively, stretch very little. In operation the elastic extension of the first pair 69 of flexible connectors facilitates relative rotational motion between the joint elements 60 and 62 in a plane generally parallel pivot plane of ankle joint 40 while the inelastic non-extension of the second pair of flexible connectors 70 prohibits relative rotational motion in a plane generally perpendicular to the pivot plane of ankle joint 40.

Figure 5A:
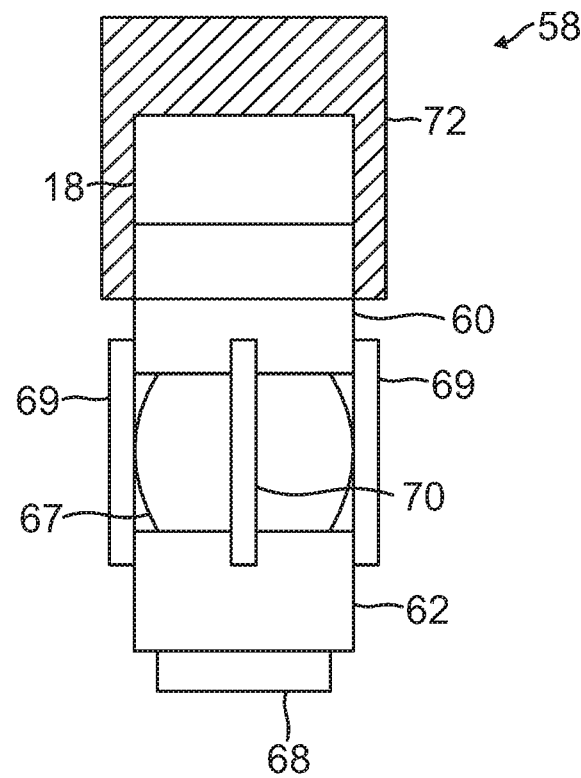
FIG. 5a is a side view of a knee joint for a leg prosthesis in accordance with an embodiment of the present invention with a locking element slidingly disposed in an unlocked position.
Figure 5B:
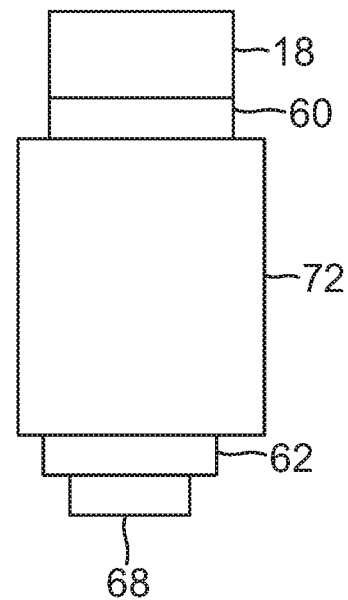
FIG. 5b is a side view of a knee joint for a leg prosthesis in accordance with an embodiment of the present invention with a locking element slidingly disposed in a locked position.
Figure 6A:
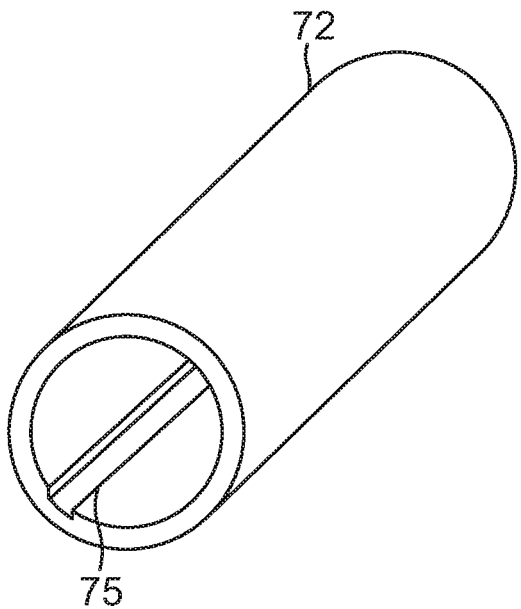
FIG. 6a is a perspective view of the locking element depicted in FIGS. 5a and 5b.
Figure 6B:
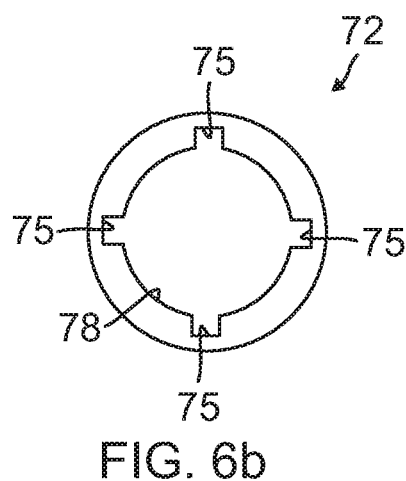

The inventor has determined that when a user is ambulatory it is preferable to prevent rotational motion of the knee joint 58 to facilitate the transfemoral leg prosthesis properly bearing the weight of the user. Accordingly, as shown in FIGS. 5*a* and 5*b* a locking element 72 is provided to prevent relative rotational motion between joint elements 60 and 62. As illustrated in these two figures the locking element 72 is slidingly disposed about either the joint element 60 as shown in FIG. 5*a* or slid down to at least partially cover both of the joint elements 60 and 62 and enclose spherical ball 67. The locking element 70 is fabricated using a three-dimensional printer. When the locking element 72 is slid up to partially cover the joint element 60 and uncover the spherical ball 67 the locking element 72 permits relative rotational motion between the joint elements 60 and 62. When the locking element is slid down to partially cover both of the joint elements 60 and 62, and enclose spherical ball 67, the locking element 72 precludes relative rotational motion between the joint elements 60 and 62. As further shown in FIGS. 6*a* and 6*b* the locking element 72 has a plurality of slots 75 formed in an inner surface 78 to accommodate sliding passage of the locking element 72 over the flexible connector pairs 69 and 70.

Figure 7:
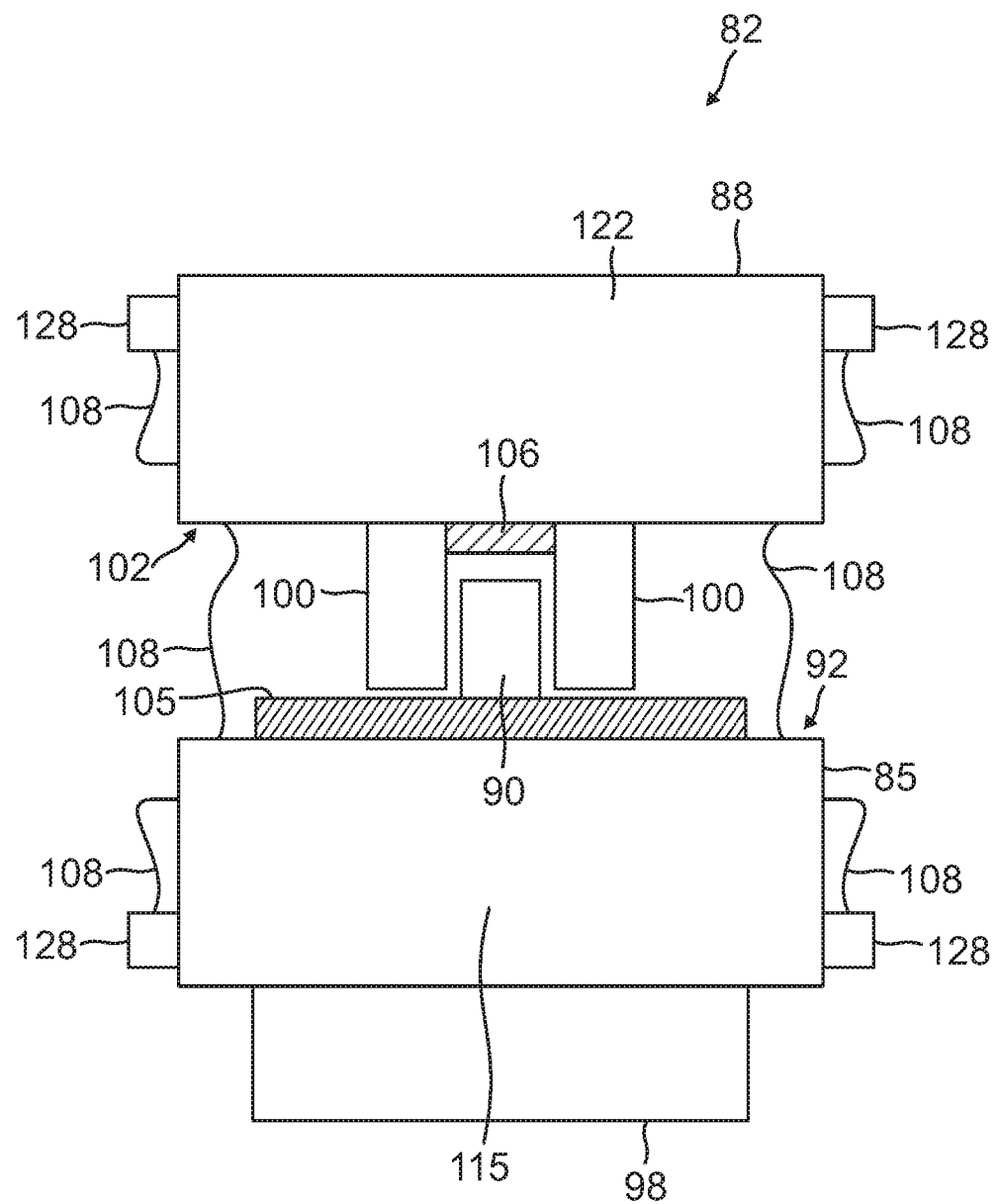
FIG. 7 is a side view of a knee joint for a leg prosthesis in accordance with another embodiment of the present invention.

Referring to FIG. 7 there is shown yet another embodiment 82 of a joint structure suitable for forming either of an ankle joint such as ankle joint 13 depicted in FIG. 1 or a knee joint such as knee joint 15 similarly depicted in FIG. 1. As shown in FIG. 7 this embodiment 82 of a joint structure comprises a first joint element 85 and a second joint element 88. Both of joint elements 85 and 88 are fabricated using a three-dimensional printer for all of the reasons discussed above. The first joint element 85 forms a generally rectangular ridge 90 at a first end 92 facing towards the second joint element 88 and forms at a second and opposing end 95 a protrusion 98 configured to fit into the recess in an adjacent modular limb element 20. Alternatively, the first joint element 85 may instead form at the second end 95 a recess configured to receive the protrusion 30 of a modular limb element 20. The second joint element 88 complementarily forms a pair of generally rectangular ridges 100 at a first end 102 facing towards the first joint element 85. The pair of ridges 100 in the first end 102 of joint element 88 are spaced apart to slidingly engage the ridge 90 at the first end 92 of the joint element 85. This sliding engagement between the ridge 90 of joint element 85 and the pair of ridges 100 of the second joint element 88 affords relative motion, including relative rotational motion, between the first joint element 85 and the second joint element 88 generally in a single plane approximately parallel to a longitudinal of the ridge 90 and pair of ridges 100. As further illustrated in FIG. 7, resilient pads 105 and 106 may be disposed between and respectively proximate the first and second joint element 85 and 88 to cushion meeting engagements of the first and second joint elements 85 and 88 and shocks that might otherwise be transmitted up the leg prosthesis when, for example, a user is walking and the leg prosthesis is bearing the users weight in a repetitive fashion. The inventor has determined that the first and second joint elements 85 and 88 have a greater operational lifetime without fracture or other failure (e.g. cracking) if these resilient pads 105 and 106 are included.

Figure 8:
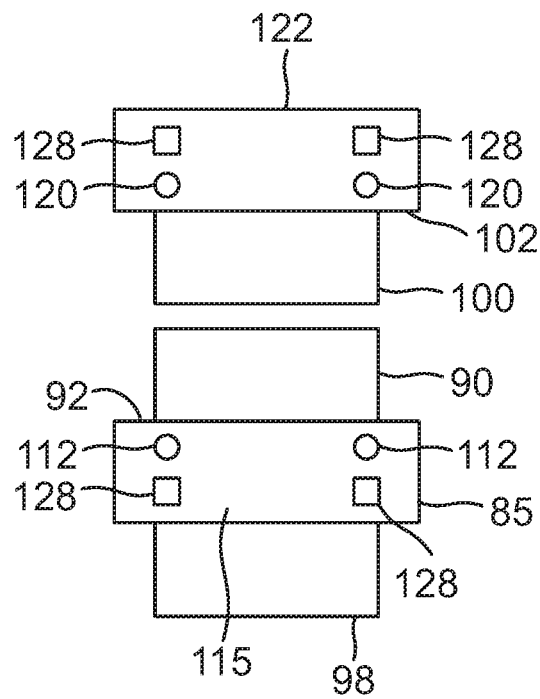
FIG. 8 is a side view of the knee joint elements depicted in FIG. 7.
Figure 9:
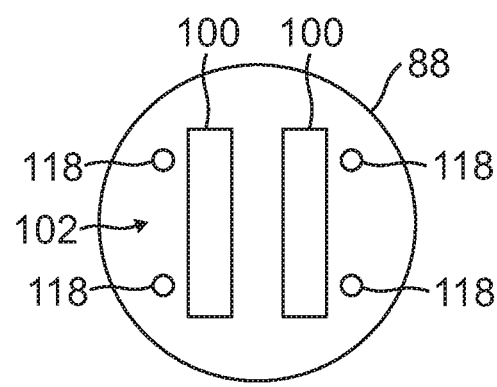
FIG. 9 is a top down and bottom up view of the knee joint elements depicted in FIGS. 7 and 8.
Figure 9:
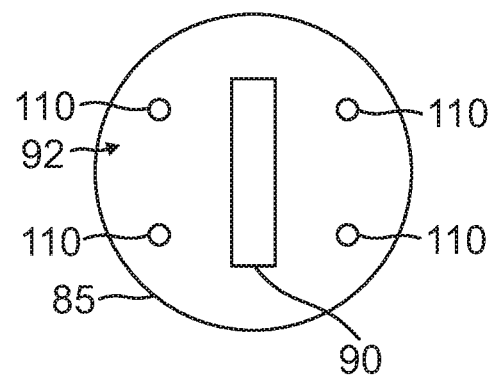

As further depicted in FIGS. 8 and 9 each of the first and second joint elements 85 and 88 further define a plurality of apertures configured to accept internal passage of complementary pairs of flexible and non-extensible connectors 108 through each of the first and second joint elements 85 and 88. As shown in FIG. 9 the first joint element 85 defines a plurality of first apertures 110 in the first end 92 of first joint element 85 and further defines a plurality of second apertures 112 in a side 115 of the first joint element 85. The corresponding apertures of the first and second plurality of apertures 110 and 112 of the first joint element 85 communicate internally through the first joint element 85 thereby allowing one of the flexible and non-extensible connectors 108 to enter the body of the first joint element 85 through one of the second apertures 112 and exit the body of the first joint element through a corresponding one of the first apertures 110. Second joint element 88 similarly and complementarily defines a plurality of first apertures 118 in the first end 102 of second joint element 88 and further defines a plurality of second apertures 120 in a side of the second joint element 88. Like the first joint element 85, the corresponding apertures of the first and second plurality of apertures 118 and 120 in the second joint element 88 also communicate internally through the second joint element 88 thereby allowing one of the flexible and non-extensible connectors 108 to enter the body of the second joint element 88 through one of the first apertures 118 and exit the body of the second joint element 88 through a corresponding one of the second apertures 120.

As will now be more fully described, removing slack from the flexible and non-extensible connectors 108 effectuates a locking of the first joint element 85 with the second joint element 88 and effectively precludes relative rotational motion between the first joint element 85 and the second joint element 88. As shown in FIG. 7 the flexible connectors 108 are attached at their ends to pairs of tensioning elements 128. These pairs tensioning elements are respectively detachably connected to either of the side 115 of the first joint element 85 and the side 122 of the second joint element 88. Accordingly, one end of each flexible connector 108 is detachably coupled at one end to the first joint element 85 and detachably coupled at another end to the second joint element 88 by the connection to a tensioning element 128. As further shown in FIG. 7 each of the flexible connectors 108 has one end secured to a tensioning element 128 detachably connected to the side 115 of the first joint element. The flexible connector 108 is then threaded from the exterior of the first joint element 85 into the body of the first joint element 85, then out of the first joint element 85 to enter into the body of the second joint element 88 and then exit the second joint element 88 to terminate at another tensioning element 128 detachably coupled to the side 122 of the second joint element 88.

More specifically the flexible connectors 108 enter into the body of the first joint element 85 through the second apertures 112 in the side 115 of the first joint element 85, exit the body of the first joint element 85 through the apertures 110 in the end 92 of the first joint element 85, enter into the body of the second joint element 88 through the apertures 118 in the end 102 of the second joint element 88 and exit the body of the second joint element through the apertures 120 in the side 122 of the second joint element, there to terminate in a tensioning element 128 attached to the exterior of the second joint element 88. The length of the flexible connectors 108 is selected so there is no slack, and preferably but not necessarily some slight tension, when the tensioning elements 128 attached to opposing ends of a flexible connector 108 are respectively connected to the first and second joint elements 85 and 88. In this configuration the flexible connectors 108 preclude relative motion, including relative rotational motion between the first and second joint elements 85 and 88. Detaching one end of each of the flexible connectors, however, permits relative motion between the first and second joint elements 85 and 88, including rotational motion. The inventor has determined this arrangement beneficially enables a user of the prosthetic leg of the present invention to bear weight without folding while further advantageously permit bending of the prosthetic leg when the user is seated. The inventor has determined that prosthetic leg users typically find sitting more comfortably if they are able to bend their prosthetic leg.

Figure 10A:
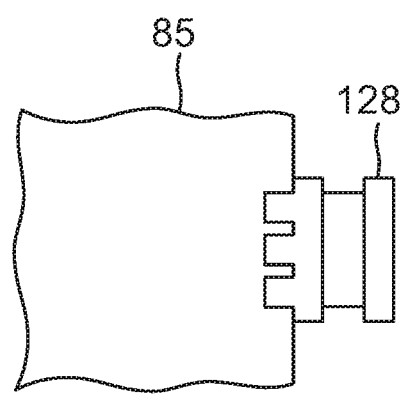
FIG. 10a is an expanded cross-sectional side view of one embodiment of a winding element detachably engaging a knee element.
Figure 10B:
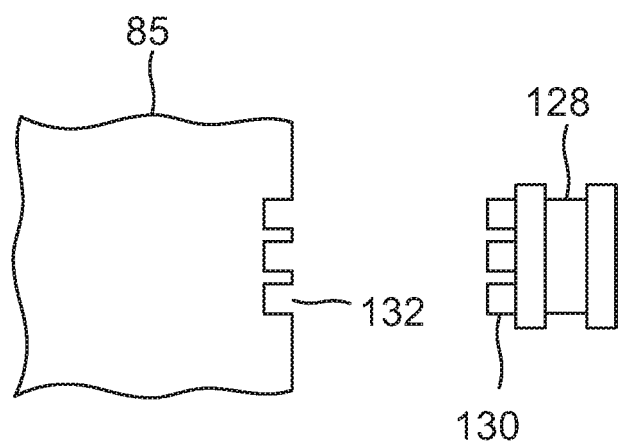
FIG. 10b is a expanded cross-sectional side view of the winding element depicted in FIG. 10a detached from the knee element.

Referring to FIGS. 10a and 10b there is shown one embodiment for detachably connecting the tensioning elements 128 to one of the sides 115 or 122 of the first and second joint elements 85 and 88. As shown, the tensioning elements may be configured to include pins 130 protruding from a side of the tensioning elements 120. The first and second joint elements 85 and 88 may then be provided with apertures 132 formed in the sides 115 and 112 of the first and second joint elements 85 and 88 to receive the pins 130 with, preferably but not necessarily, a tight fit. Attaching the pair of tensioning elements 128 respectively attached to ends of a flexible connector 108 to the first or second joint elements 85 and 88 then prevents and slack from forming in the flexible connector.

Figure 11A:
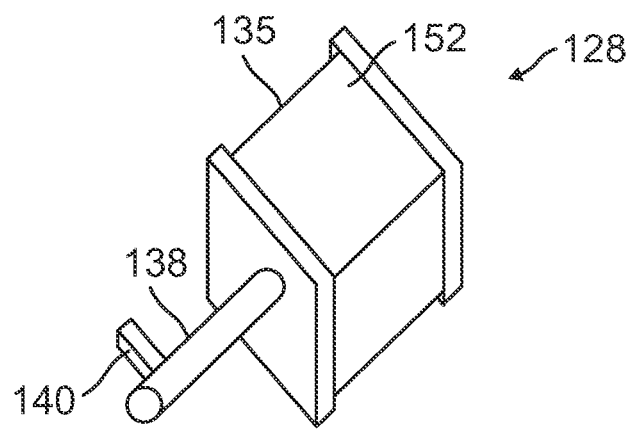
FIG. 11a is a perspective view of a second embodiment of a winding element configured for rotatingly engaging a knee element.
Figure 11B:
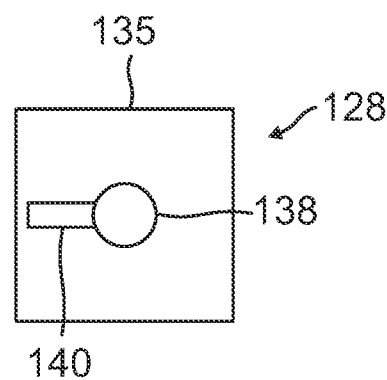
Figure 12A:
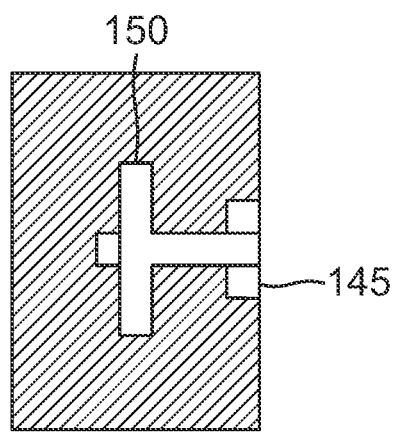
FIG. 12a is an expanded cross-sectional view of a knee element of the present invention configured to accept the winding element depicted in FIGS. 11a and 11b.
Figure 12B:
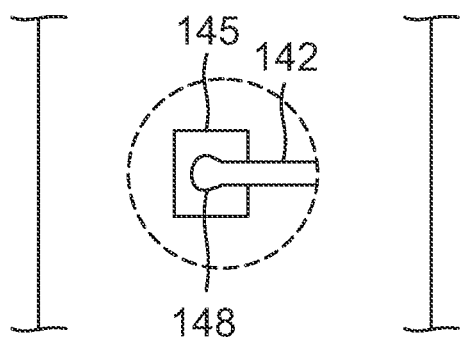

Referring to FIGS. 11a, 11b, 12a and 12b there is shown an alternative embodiment wherein the tensioning elements 128 are rotatably coupled to the first and second joint elements 85 and 88. In this embodiment, as shown in FIGS. 11a and 11b the tensioning element has a "key" structure including a generally square base portion 135, a generally circular key portion 138 protruding from a side of the base portion 135 and a tooth portion 140 attached to the key portion 138 and oriented generally perpendicular to the key portion 138. As shown in FIG. 12b the first and second joint elements 85 and 88 are provided along one side with several nested apertures including a slot 142 configured to slidingly receive the tooth portion 140 of the tensioning element 128, a first aperture 145 configured to receive at least a portion of the generally square base portion 135 of the tensioning element 128 in a non-rotatable engagement and a second aperture 148 configured to accept the circular key portion 138. As further illustrated in FIG. 12a the first and second joint elements 85 and 88 are further provided with a generally circular cavity 150 configured to accommodate rotational movement of the tooth portion 140 while inserted into the first and second joint elements 85 and 88. In operation an end of a flexible connector is attached to a side 152 of an individual tensioning element. The key portion 138 and tooth portion 140 of the tensioning element 128 are rotatingly disposed within the circular cavity 150 of the first or second joint element 85 or 88 and retained therein unless the tooth portion 140 aligns with the slot 142. When a user desires to lock the joint elements 85 and 88 the tensioning element is rotated until the flexible connector becomes taught. At least part of the base portion of the tensioning element 128 is then inserted into the first aperture where the tensioning element is precluded from rotating with respect to the joint element 85 or 88 thereby precluding loosening of the flexible connector. When bending of the knee joint of the leg prosthesis is desired by a user the base portion of the tensioning element 128 is removed from the aperture 145 and the flexible connector can be permitted to grow slack so as to accommodate bending of the leg prosthesis.

The prosthetic leg embodiments of the present invention that have been discussed above provide a relatively inexpensive prosthetic that can be custom manufactured by merely altering the number of modular elements employed or by scaling the dimensions of those modular elements, the latter being a relatively simple process since the modular elements are fabricated by three-dimensional printing. It will be appreciated by those skilled in the relevant arts that the prosthetic leg embodiments of the present invention can be modified in arrangement and detail to provide numerous other embodiments that do not depart from the spirit and scope of this invention. Accordingly, all equivalent relationships to those illustrated in the drawings and described in this specification are intended to be encompassed within the scope of the present invention, as set forth in the claims below and equivalents thereof.

Figure 13:
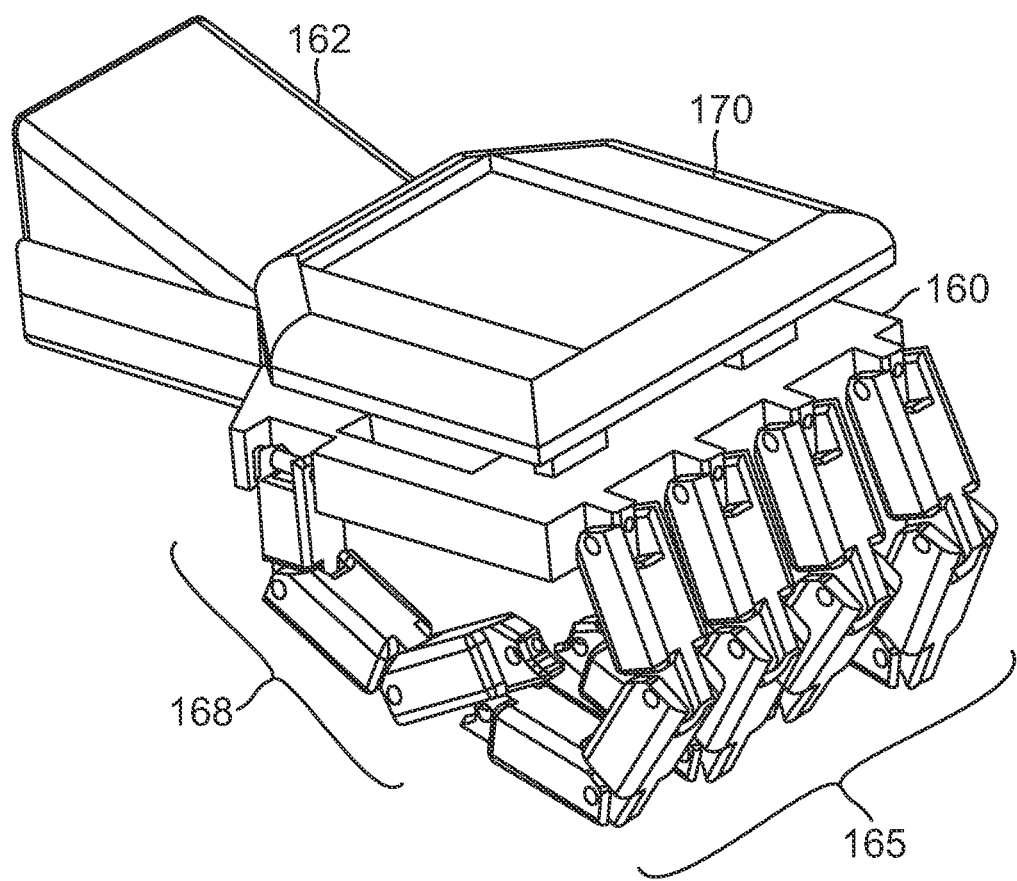
FIG. 13 is a perspective view of a prosthetic hand in accordance with one embodiment of the present invention with the finger elements arranged in a closed position.
Figure 14:
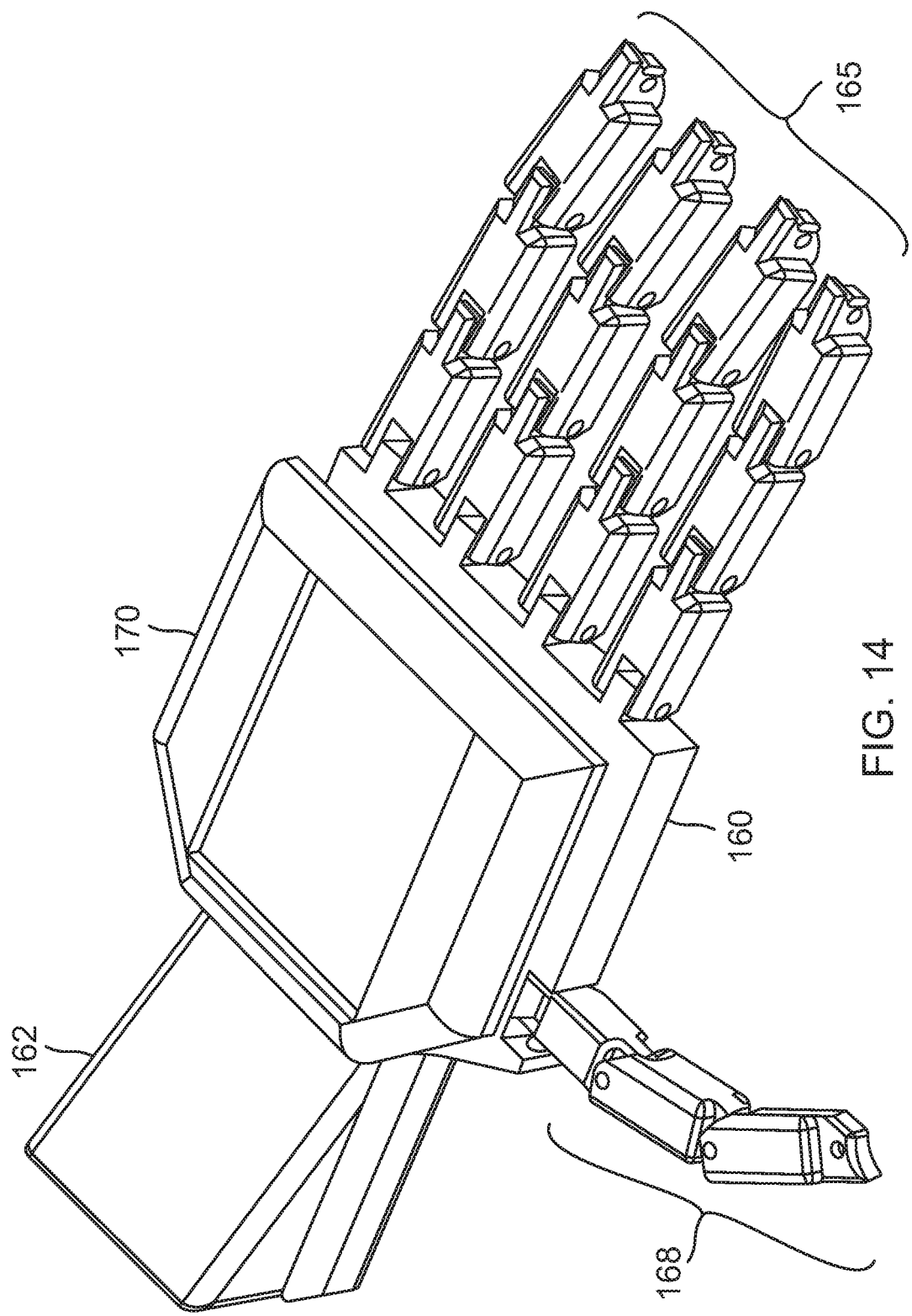
FIG. 14 is a perspective view of a prosthetic hand in accordance with one embodiment of the present invention with the finger elements arranged in an open position.

Referring to the figures, and more particularly FIGS. 13 and 14 thereof, there is shown one embodiment of the prosthetic hand 158 of the present invention. The prosthetic hand 158 of the present invention includes a base element 160 attached at one end to a wrist element 162. The wrist element 162 has one end opposite the end connected to the base 160 that is configured to receive the outer extremity of an amputated hand, a plurality of prosthetic fingers 165 (generally delineated in FIGS. 13 and 14) pivotally attached to the base 160. In one preferred embodiment the prosthetic hand 158 further includes a prosthetic thumb 168 comprised of modular elements. The prosthetic thumb 168 is configured to rotate in two generally perpendicular planes, thereby mimicking the axes of rotation of a natural thumb. As further depicted in FIGS. 13 and 14 the prosthetic hand 158 included further elements discussed more fully below that enable the prosthetic fingers 165 and thumb 168 to move from a closed configuration, as depicted in FIG. 13, to an open configuration as depicted in FIG. 14. These further elements include an actuator mounted on the base 160, a controller for activating and deactivating the actuator and flexible connectors having one end attached to the base and second end attached to the actuators. A cover element 170 is attached to the base 160. This cover 170 obscures view of the electro-mechanical workings mounted on the base 160 affords those elements some degree of protection from accidental harm.

As discussed above in connection with the modular prosthetic leg embodiment on the present invention a vital aspect of the present invention is the modular character of the various elements forming the hand prosthesis of the present invention. Another vital is use of three-dimensional printing devices and three-dimensionally printing techniques to fabricate the modular elements comprising the prosthesis of the present invention. These aspects of the present invention present numerous advantages and cost savings discussed more fully above in this specification.

Figure 15:
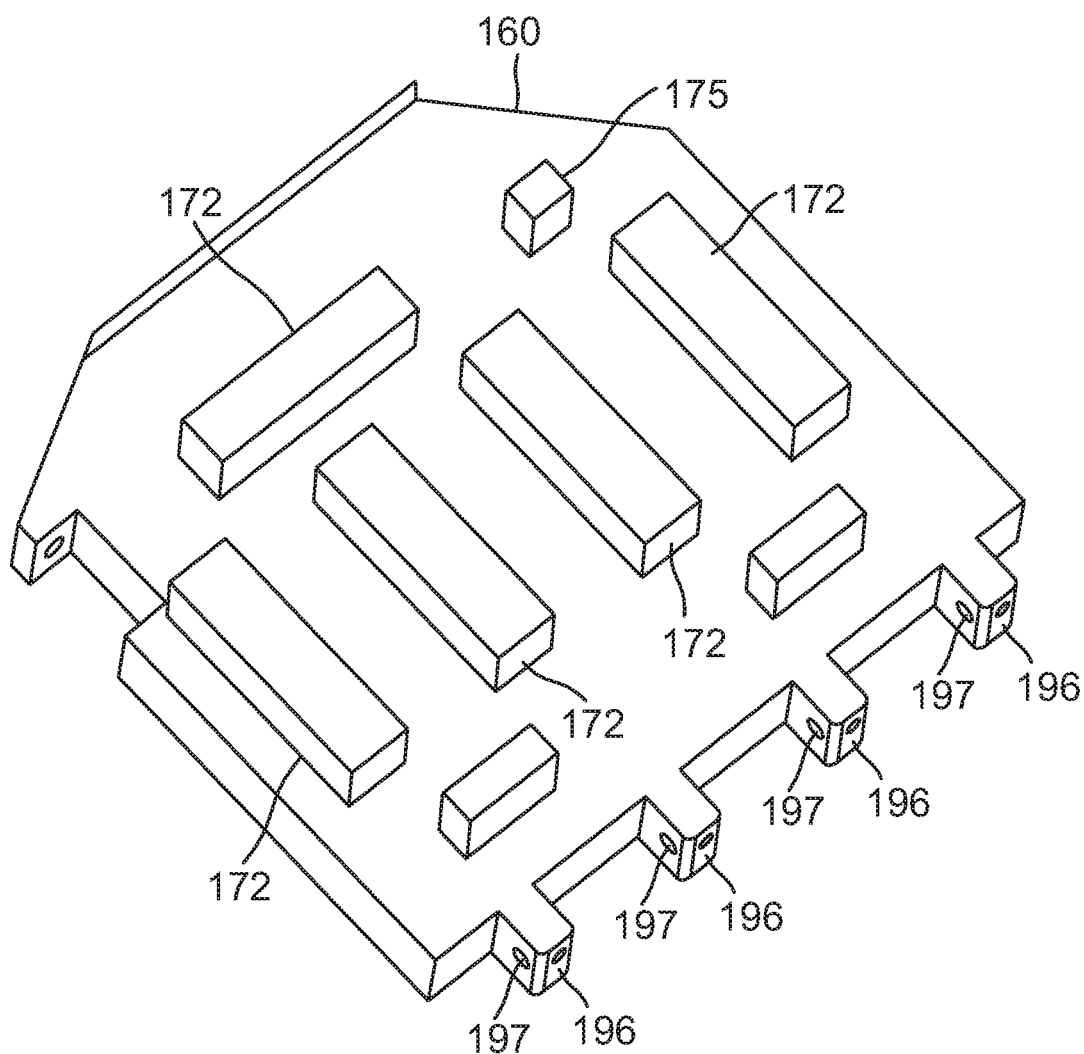
FIG. 15 is a perspective view of a base element for the prosthetic hand depicted in FIGS. 13 and 14.

Referring to FIG. 15 there is shown the base 160 and elements mounted thereon. These elements include actuators 172. In one preferred embodiment of the present invention each prosthetic finger 165 and the prosthetic thumb 168 is provided with its own actuator. In other embodiments, however, movement of all the prosthetic fingers 165 from open to closed positions could achieved with a single one of the actuators 172. This single actuator could also be coupled to the prosthetic thumb 168 to simultaneously effectuate opening and closing of all the prosthetic fingers 165 and the prosthetic thumb 168 essentially in concert. Alternatively, all of the prosthetic fingers 165 could be coupled to a first actuator 172 and the prosthetic thumb 168 could be coupled to a second actuator 172.

The inventor has determined numerous benefits exist for applications where the independent activation of individual prosthetic fingers 165 is provided, as opposed to applications affording only collective control of all of the prosthetic digits. The latter is an unavoidable consequence of using of only a single actuator. For example, it is known that have a remarkable capacity for so-called "two finger typing" where only one digit from each hand is employed to press keys on a keyboard. The inventor has determined that typing on a keyboard using a prosthetic hand is far more easily performed if only a single prosthetic finger is extended from the prosthetic hand 158 compared to prosthetics providing only collective control of all the prosthetic fingers as a single integrated unit; as would result of only a single actuator 172 is employed. In such single actuator 172 embodiments the user's only option is to have all of the prosthetic fingers extended. The user is then only able to use the longest of these extended prosthetic fingers (typically the middle finger) to press upon the keyboard. The inventor has further found that numerous circumstances exist where the ability to "pinch" an object between thumb and forefinger, as opposed to grasping with all of one's fingers, are ubiquitous and typically overlooked by persons who are not amputees and, therefore, deprived of the ability to perform this function. Picking up a piece of paper, for example, is a common and commonly overlooked "pinching" action. Accordingly, in view of the inventor's discoveries, affording the ability to perform extension of only a single prosthetic finger, and to perform "pinching" motions involving an amputee's use of only a prosthetic forefinger and prosthetic thumb, are highly desirable and within the scope of the present invention. In one embodiment of the present invention at least two actuators 172 are provided on the base 160. One of these actuators 172 may be collectively connected to all of the prosthetic fingers 165 and the prosthetic thumb 168, while the second actuator 172, in accordance with this embodiment of the present invention the present invention, would be attached to only the user's forefinger. This arrangement would enable independent extension of the user's forefinger, separate and apart from the remaining prosthetic fingers 165. In yet another embodiment of the present invention a first actuator 172 may be coupled to all of the user's prosthetic fingers 165 and prosthetic thumb 168, for grasping purposes, and a second actuator 172 is coupled to only the user's prosthetic forefinger and prosthetic thumb 168, thereby affording actions "pinching" actions with the prosthetic hand 158 in addition to grasping actions afforded by the first actuator 172.

In addition to the actuators 172 there is a controller 175 mounted on the base 160 and electronically connected to the actuators 172. This controller 175 is configured to signal the actuators 172 to activate upon receipt of a signal, the latter as discussed more fully below. In one embodiment of the prosthetic hand of the present invention an Arduino® controller is employed. A power supply (not illustrated) for the controller 175 and the actuators 172 may also be removably affixed to the base 160. In one embodiment this power supply is a conventional nine-volt battery.

Referring to FIGS. 16*a* and 16*b* there is shown the cover 170 for the prosthetic hand embodiment 158 of the present invention. The cover may, but need not, entirely cover the entirety of the base 160. One preferred embodiment of the cover 170 shown in FIGS. 16*a* and 16*b* includes struts 178 to attach the cover to the base 160 and further position the cover 170 above components having moving parts, such as for example the actuators 172, mounted on the base 160. The cover 170 may further form an indentation 179 within which to mount user controls to signal the controller to activate the actuators 172 and effectuate opening or closing of the prosthetic fingers 165 and thumb 168.

Referring to FIGS. 17*a*, 17*b* and 17*c* there is illustrated several views of a modular finger element 180 of the present invention. The finger element 180 forms at one end a ridge 182 and forms at an opposing end a slot 185 spaced to accommodate the ridge 182 of an adjacent finger element in a sliding relationship. That is, adjacent finger elements can rotate with respect to one another little resistance imposed by the ridge 182 of one finger element 180 engaging the slot 185 of an adjacent finger element. The ridge 182 further defines a circular opening 188 transverse to a longitudinal axis of the finger element 180. The sides of the opposing end of the finger element 180 further define a similarly oriented pair of openings 190 positioned so that, when the ridge 182 of an adjacent finger element is positioned in the slot 185 of the finger element 180 the three circular openings are aligned. This arrangement is to accommodate a pivot pin (not shown) to retain the adjacent finger elements in proximity to one another and facilitate relative rotational motion between the adjacent finger elements. As shown in FIGS. 17a and 17b each of the ridge 182 forms a partially curved surface 192 along a lower portion of an end of the ridge 182. The opposing end of the finger element further defines a curved surface 195 along a lower portion of the finger element 180. This configuration of curved surfaces 192 and 195 permits relative rotational motion between adjacent finger elements in only one direction, thus mimicking the freedom of motion of a natural finger. Referring to FIG. 15 there are shown at one end of the base 160 a plurality of ridges 196 projecting from an end of the base 160 opposite the wrist element 162. In a preferred embodiment there are four such ridges, corresponding to the conventional number of fingers on a person's hand. These ridges 196 have essentially the same dimensions as the ridges 182 on the modular finger elements 180. Each of these ridges further defines a transverse bore 197 disposed in the ridges 196 at approximately the same relative location as the circular openings 188 in the ridges of the modular finger elements 180. These ridges accommodate the slots 185 of modular finger elements 180 and afford the means by which the prosthetic fingers 165 are pivotally attached to the base 160 as shown, for example in FIGS. 13 and 14.

Figure 17D:
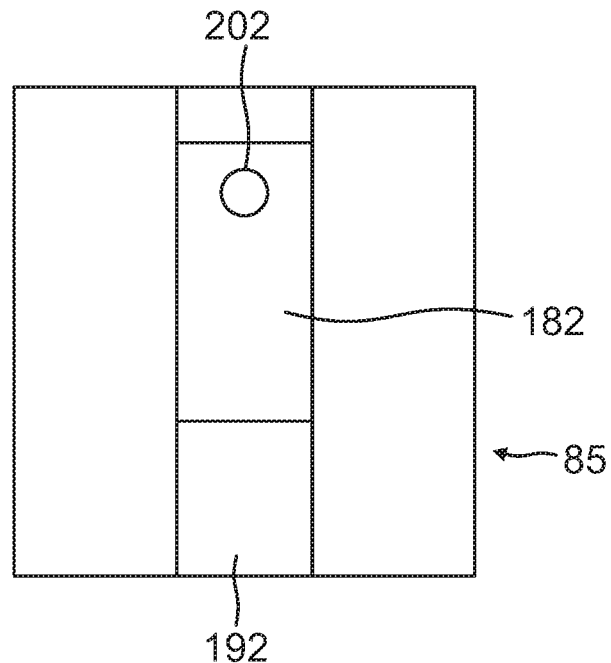
FIG. 17d is a front view of the modular finger element depicted in FIGS. 17a-c.
Figure 17E:
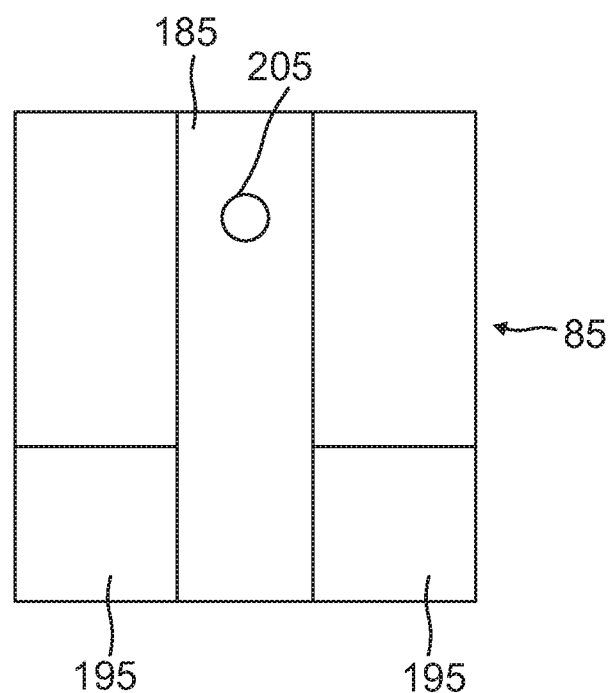
FIG. 17e is a rear view of the modular finger element depicted in FIGS. 17a-d.

As shown in FIG. 17c a lower surface of the finger elements 180 define a pair of apertures 198 and 200 at opposing ends of the finger element 180. As discussed more fully below these apertures are essential to achieving curving of the finger elements 180 to cause the prosthetic hand 158 to shift from an open to closed position. Another feature essential to achieving curving of the finger elements 180 is depicted in FIGS. 17d and 17e. These two figures respectively depict a forward and rearward view of a finger element 180. As shown each of these opposing ends of the finger element 180 each further define a first aperture 202 in the front ends of the finger elements 180 and a second aperture 205 in the rearward ends of the finger elements 180. In a preferred embodiment these apertures 202 and 205 connect with one another so that a flexible element passing into a finger element 180 through one of these two apertures 202 and 205 can exit the finger element 180 through the other.

Figure 18:
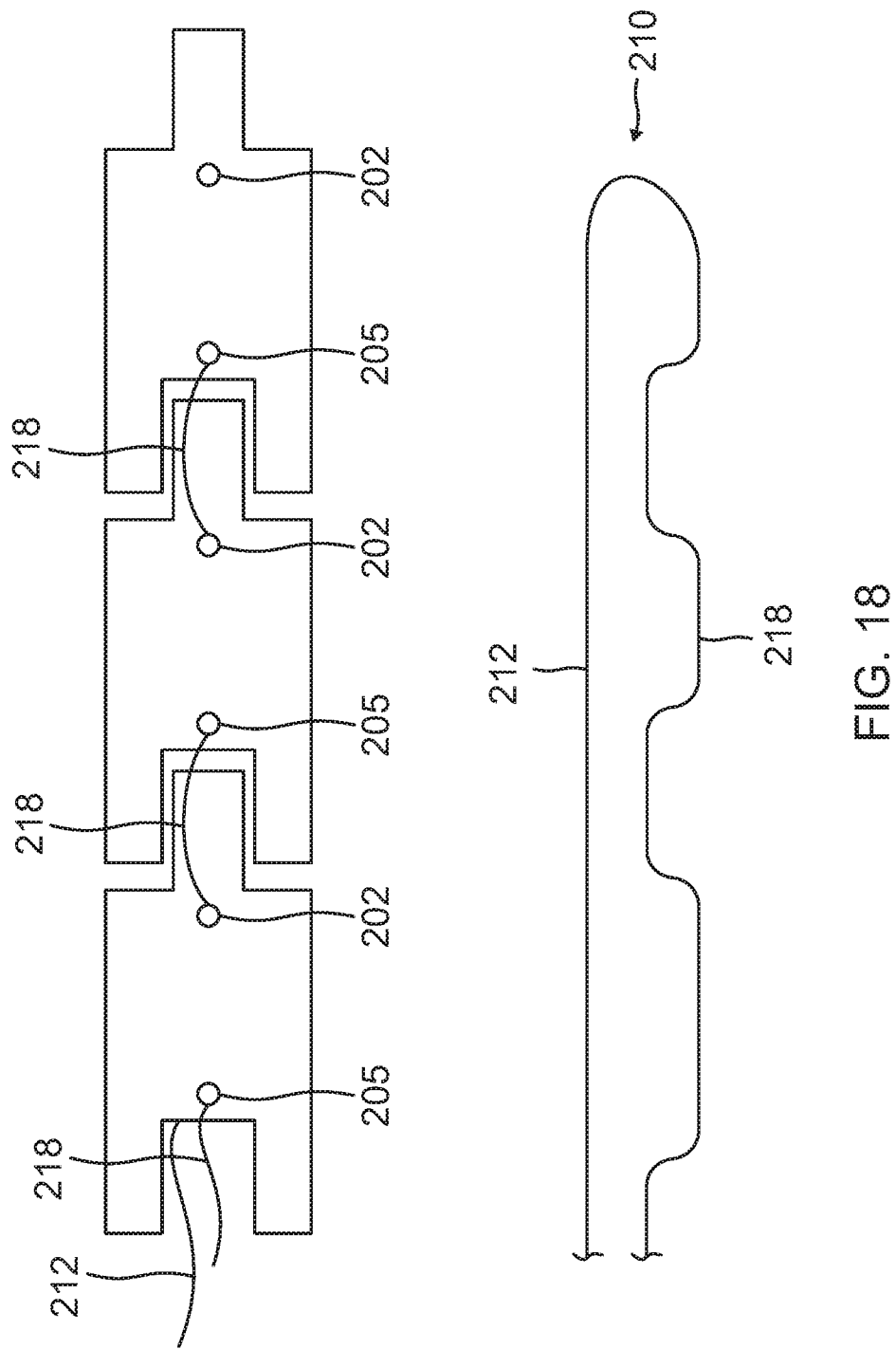
FIG. 18 is a bottom up view of a three-dimensionally printed modular figure structure for the prosthetic hand depicted in FIGS. 13 and 14.

Referring to FIG. 18 there is shown a flexible connector 210 effectuating curling of the prosthetic fingers 165 and prosthetic thumb 168. A flexible connector 210 is associated with each prosthetic finger 165 intended to curl and the prosthetic thumb 168. The flexible connector 210 may be composed of any of the materials discussed above concerning flexible connectors employed in connection with the prosthetic leg embodiment of the present invention. The flexible connector 210 can be considered to have a first portion 212 attached at one end to the base 160 and disposed through the rotationally attached modular elements 180 forming a prosthetic finger 165 through the apertures 202 and 205 of the modular elements 180. The flexible connector 210 additionally has a second portion 218 threaded into and out of the modular elements 180 through the apertures 198 and 200 disposed at the bottom of the modular elements 180. The second portion 218 is connected to the actuator 172. In operation, in one preferred embodiment of the present invention, activation of the actuator 172 draws the second portion 218 of the flexible connector 210 towards the base 160. Shorting the effective length of the flexible connector 210 within the modular elements 180 combined with the second portion 218 being threaded into and out of the modular elements 180 causes respective modular elements adjacent to one another to rotate with respect to one another, thereby causing the prosthetic fingers 165 to transition from an open configuration as depicted in FIG. 14 to a closed configuration as depicted in FIG. 13.

Figure 19:
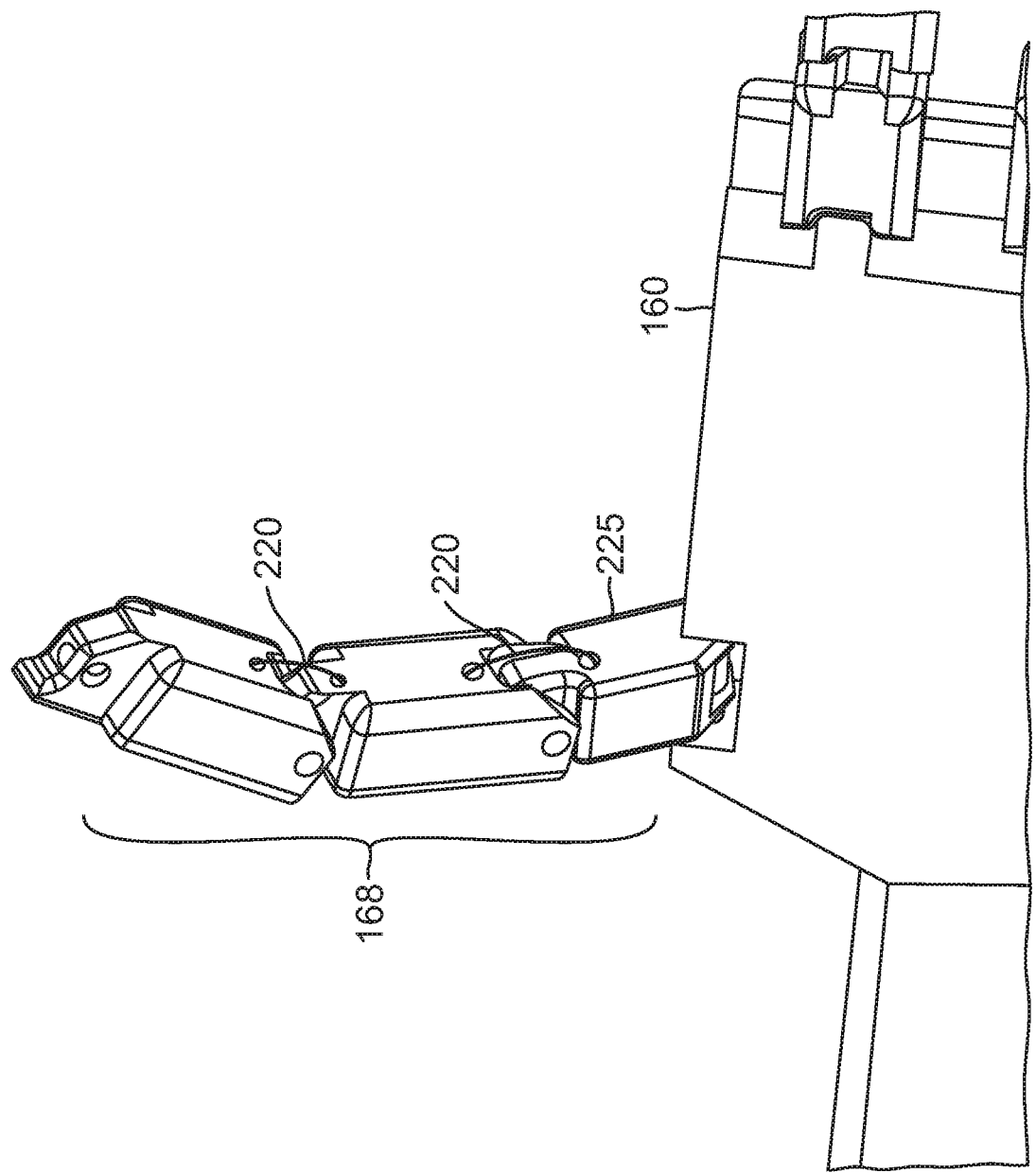
FIG. 19 is a perspective view of a three-dimensionally printed modular thumb structure for the prosthetic hand depicted in FIGS. 13 and 14.
Figure 20:
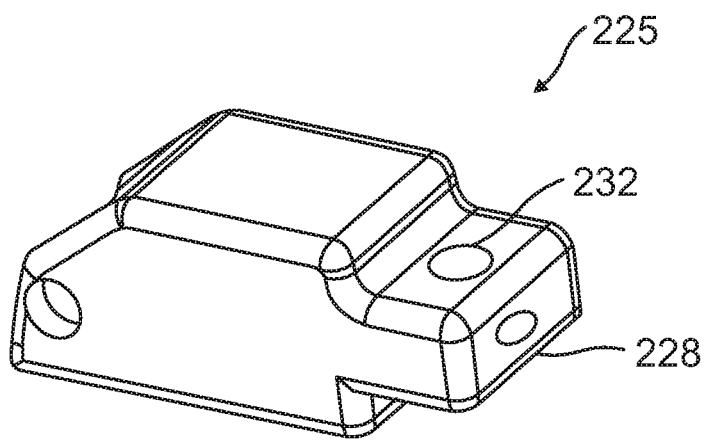
FIG. 20 is a perspective view of a three-dimensionally printed modular thumb element for the prosthetic hand depicted in FIGS. 13 and 14.

A similar arrangement of a flexible connector 220 partially disposed within and external to modular elements comprising the prosthetic thumb 168 similarly effectuates curvature from an open to a closed configuration of the prosthetic thumb. As further depicted in FIG. 19, however, the prosthetic thumb 186 rotates in two separate planes to mimic the natural motion of a natural thumb. This rotational motion of the prosthetic thumb is effectuated by a dedicated modular thumb element 225 shown in FIG. 20 and the manner in which this modular thumb element 225 is attached to the base as depicted in FIG. 19. As shown in FIG. 19 the modular thumb element 225 is pivotally attached to the base portion 160 so as to form an axis of rotation generally perpendicular to the rotational axes of the prosthetic fingers 165. Additionally, the modular thumb element 225 forms a ridge 228 configured to slidingly fit into a slot 185 of a modular finger element 180. The ridge 228, however, is oriented perpendicular to a slot formed in the rear of the modular thumb element 255. The ridge 228 further defines a bore 232 extending through the ridge 228 to rotatably couple the thumb element of an adjacent modular element 180, but this bore 232 is similarly oriented perpendicular to the axis of rotation of the thumb element 225 with respect to the base 160. In operation this configuration causes the thumb to pivot out of a plane formed by the alignment of the prosthetic fingers 165 and then curl the prosthetic thumb 168 in a fashion more closely resembling the motion of an uninjured human thumb when an actuator 172 is activated to draw the flexible coupler 220 into the base 160.

Control of the prosthetic hand 158 from an open to closed configuration, and back again, as depicted in FIGS. 13 and 14 is afforded by a user sending signals to the controller 175. In one embodiment of the present invention a touch-sensitive or pressure-sensitive controls (not shown) may be in electrical contact with the controller 175. In an alternative embodiment employing a Arduino® controller it is possible for the Arduino controller to communicate wirelessly with a smart phone 240 as shown in FIG. 13. In this embodiment it is therefore practicable to develop a smart phone app that will wirelessly communicate with the Arduino controller and respond to touch input to the screen 242 of the smart phone 240. The inventor has determined that some users find it cumbersome to access a touch or pressure sensitive controls on the prosthetic hand they intend to activate.

A further issue concerns grip control. It is known in the art to attach pressure sensors on the tips of prosthetic fingers to modulate grip and to signal prosthetic fingers to cease closure. This approach is not inexpensive, however. Further these pressure sensors can be subject to failure and damage, thus depriving a prosthetic hand user from using their prosthetic hand to safely grip fragile objects, and potentially damaging their prosthesis if gripping a more rugged object. The present invention, however, affords a more innovative approach to grip control. The inventor has determined grip strength can be effectively limited by judicious selection of the material for the flexible connectors 210 and 220. By selection of a material for the flexible connectors 210 and 220 having sufficient elasticity and elongation, the maximum grip force applied will be determined by the preset length of travel of the flexible connectors 210 and 220 caused by the actuators 172 multiplied by the spring constant of the material comprising the flexible connectors 210 and 220. Selection of an appropriate material can then prevent harm arising either excessive grip strength or attempts to grasp an object larger than the closed position of the prosthetic hand.

As demonstrated in the detailed description above the present invention affords a prosthetic limb suitable for use in remote locations having access to a three-dimensional printer. Because of the modular nature of the components comprising the prosthetic limb of the present invention, replacement of the entire prosthetic limb of the present invention is not necessitated when a component is damaged or otherwise fails. Instead, the damaged or failed modular component can be three-dimensionally reprinted and replaced.

Having described and illustrated the present invention in various preferred embodiments, it should be readily apparent that the present invention can be modified in arrangement and detail without departing from the scope of this invention. It is to be realized that the relationships of the various parts of the present invention in regard to size, shape, form materials, function and the manner of operation, assembly and use thereof can be modified in various ways, as will be readily apparent to those skilled in the art, without departing spirit and scope of the present invention. The present invention is further capable of other embodiments and of being practiced and carried out in various alternate ways without departing from the scope of the present invention. Accordingly, all equivalent relationships to those illustrated in the drawings and described in the specification above are intended to be encompassed within the scope of the present invention.

It is to be further understood that the phraseology and terminology employed herein are for the purposes of description only and should not be regarded as limiting the scope of the present invention. Therefore, the foregoing description of the present invention is to be considered as illustrative only of the principles of the present invention. Further, since numerous modifications, changes and alternative embodiments will occur to those skilled in the art, the present invention is not to be limited to the structures, elements, construction and operation shown and described above, but solely by the claims set forth below and equivalents thereof.

What is claimed is:

1. A prosthetic appendage for attachment to an outer extremity of an amputated limb, comprising:
    a base element wherein the base element forms a foot structure to support walking upon the prosthetic appendage;
    a plurality of three-dimensionally printed modular limb elements forming a protrusion at a first end and forming at a second and opposing end a recess to receive the protrusion from an adjacent three-dimensionally printed limb element;
    a sphere;
    a first three-dimensionally printed modular limb element having an end pivotally connecting to the base element and forming at a first end a depression configured to receive a portion of the sphere and forming at a second and opposing end a protrusion or a recess to engage another of the plurality of three-dimensionally printed limb elements;
    a second three-dimensionally printed joint element forming at a first end a recess to receive a portion of the sphere; and
    a third three-dimensionally printed modular limb element having an end configured to receive the outer extremity of the amputated limb instead of engaging an adjacent limb element.

2. The prosthetic appendage of claim 1 further comprising:
    at least a pair of flexible and non-extensible connectors attached to opposing sides of the first and the second joint elements generally perpendicular to a pivot plane; and
    at least a pair of flexible and elastically extensible connectors attached to opposing sides of the first and the second joint elements generally parallel to the pivot plane.

3. The prosthetic appendage of claim 1 further comprising a prosthetic knee structure including:
    a first three-dimensionally printed knee element forming at a first end a ridge and forming at a second and opposing end a protrusion or recess to engage an adjacent one of the plurality of limb elements, the first knee element further defining a plurality of apertures at the first end and in a side of the first knee element, the apertures at the first end communicating with the apertures formed in the side;
    a second three-dimensionally printed knee element forming at a first end a pair of ridges spaced apart to slidingly receive the ridge of the first knee element and forming at a second and opposing end a protrusion or recess to engage an adjacent one of the plurality of limb elements, wherein the sliding engagement of the ridge of the first knee element between the pair of ridges of the second knee element affords relative motion between the first and second knee elements in generally a single plane, the second knee element further defining a plurality of apertures at the first end and in a side of the second knee element, the apertures at the first end communicating with the apertures formed in the side;
    a plurality of tensioning elements respectively and detachably attached to the first and second knee elements;
    a plurality of flexible and non-extensible connectors respectively attached at opposing ends to pairs of the tensioning elements, a first tensioning element of a pair being detachably attached to the first knee element and a second tensioning element of a pair being detachably attached to the second knee element, the flexible and non-extensible connectors being further threaded through the apertures of the first and second knee elements, wherein relative motion of the first and second knee elements is prohibited when the flexible connectors are tensioned by the pair of tensioning elements being attached to the first and second knee elements, and wherein relative motion of the first and second knee elements is permitted when the flexible connectors are slack.

4. The prosthetic appendage of claim 1 further comprising a prosthetic knee structure including:
    a first three-dimensionally printed knee element forming at a first end a ridge and forming at a second and opposing end a protrusion or recess to engage an adjacent one of the plurality of limb elements,
    a second three-dimensionally printed knee element forming at a first end a pair of parallel ridges spaced apart to slidingly receive the ridge of the first knee element and further forming at a second and opposing end a protrusion or recess to engage an adjacent one of the plurality of limb elements, wherein sliding engagement of the ridge of the first knee element between the pair of ridges of the second knee element affording relative motion between the first and second knee elements in generally a single plane;

at least one flexible and elastically extensible connector attached to and disposed internally in each of the first and second knee elements; and a locking element slidingly disposed about the first and second knee elements, wherein the locking element prohibits relative motion between the first and second knee elements when positioned about both the first and second knee elements and permits relative motion between the first and second knee elements when positioned about only one of the first and second knee elements.

5. A prosthetic leg for attachment to an outer extremity of an amputated leg, comprising:

a foot element;

a plurality of modular and three-dimensionally printed limb elements forming a protrusion at a first end and forming at a second and opposing end a recess configured to receive the protrusion from an adjacent limb element;

a sphere;

a first three-dimensionally printed ankle element being pivotally attached to the foot element by being shaped at a first end to receive a portion of the sphere and forming at a second end a protrusion or recess to engage another of the plurality of three-dimensionally printed limb elements;

the foot element further including an upper surface shaped to receive a portion of the sphere; and at least one of the three-dimensionally printed limb elements forming at one end a cavity configured to receive the outer extremity of the amputated leg.

6. The ankle joint of claim 5 further comprising:

at least a pair of non-extensible and flexible connectors attached at first ends to opposing sides of the first ankle element generally perpendicular to a pivot plane, and further attached at second ends to the upper surface of the foot element; and at least a pair of flexible and elastically extensible connectors attached to opposing sides of the first ankle element generally parallel to the pivot plane, and further attached at second ends to the upper surface of the foot element.

7. The prosthetic appendage of claim 5 further comprising a prosthetic knee structure including:

a first three-dimensionally printed knee element forming at a first end a ridge and forming at a second and opposing end a protrusion or recess to engage an adjacent one of the plurality of limb elements, the first knee element further defining a plurality of apertures at the first end and in a side of the first knee element, the apertures at the first end communicating with the apertures formed in the side;

a second three-dimensionally printed knee element forming at a first end a pair of ridges spaced apart to slidingly receive the ridge of the first knee element and forming at a second and opposing end a protrusion or recess to engage an adjacent one of the plurality of limb elements, wherein the sliding engagement of the ridge of the first knee element between the pair of ridges of the second knee element affords relative motion between the first and second knee elements in generally a single plane, the second knee element further defining a plurality of apertures at the first end and in a side of the second knee element, the apertures at the first end communicating with the apertures formed in the side;

a plurality of tensioning elements respectively and detachably attached to the first and second knee elements;

a plurality of flexible and non-extensible connectors respectively attached at opposing ends to pairs of the tensioning elements, a first tensioning element of a pair being detachably attached to the first knee element and a second tensioning element of a pair being detachably attached to the second knee element, the flexible and non-extensible connectors being further threaded through the apertures of the first and second knee elements, wherein relative motion of the first and second knee elements is prohibited when the flexible connectors are tensioned by the pair of tensioning elements being attached to the first and second knee elements, and wherein relative motion of the first and second knee elements is permitted when the flexible connectors are slack.

8. The prosthetic appendage of claim 5 further comprising a prosthetic knee structure including:

a first three-dimensionally printed knee element forming at a first end a ridge and forming at a second and opposing end a protrusion or recess to engage an adjacent one of the plurality of limb elements, the first knee element further defining a plurality of apertures at the first end and in a side of the first knee element, the apertures at the first end communicating with the apertures formed in the side;

a second three-dimensionally printed knee element forming at a first end a pair of ridges spaced apart to slidingly receive the ridge of the first knee element and forming at a second and opposing end a protrusion or recess to engage an adjacent one of the plurality of limb elements, wherein the sliding engagement of the ridge of the first knee element between the pair of ridges of the second knee element affords relative motion between the first and second knee elements in generally a single plane, the second knee element further defining a plurality of apertures at the first end and in a side of the second knee element, the apertures at the first end communicating with the apertures formed in the side;

a plurality of tensioning elements respectively and rotatingly coupled to the first and second three-dimensionally printed knee elements; and a plurality of flexible and non-extensible connectors respectively attached at opposing ends to pairs of the tensioning elements, a first tensioning element of a pair being detachably attached to the first knee element and a second tensioning element of a pair being detachably attached to the second knee element, the flexible and non-extensible connectors being further threaded through the apertures of the first and second knee elements, wherein relative motion of the first and second knee elements is prohibited when the flexible connectors are tensioned by the pair of tensioning elements being attached to the first and second knee elements, and wherein relative motion of the first and second knee elements is permitted when the flexible connectors are slack.

9. The prosthetic appendage of claim 5 further comprising a prosthetic knee joint including:

a second sphere;

a first three-dimensionally printed knee joint element forming at a first end a depression configured to receive a portion of the second sphere and forming at a second and opposing end a protrusion or a recess to engage another of the plurality of three-dimensionally printed limb elements; and a second three-dimensionally printed knee joint element forming at a first end a recess to receive a portion of the second sphere;

at least a pair of flexible and non-extensible connectors attached to opposing sides of the first and the second joint elements generally perpendicular to a pivot plane;

at least a pair of flexible and elastically extensible connectors attached to opposing sides of the first and the second joint elements generally parallel to the pivot plane, and a locking element slidingly disposed about the first and second knee elements, wherein the locking element prohibits relative motion between the first and second knee elements when positioned about both the first and second knee elements and permits relative motion between the first and second knee elements when positioned about only one of the first and second knee elements.

\* \* \* \* \*